United States Patent [19]

Fontaine

[11] Patent Number: 5,370,683
[45] Date of Patent: Dec. 6, 1994

[54] VASCULAR STENT

[75] Inventor: Arthur B. Fontaine, Fresno, Calif.

[73] Assignee: Cook Incorporated, Bloomington, Ind.

[21] Appl. No.: 192,064

[22] Filed: Feb. 4, 1994

Related U.S. Application Data

[63] Continuation of Ser. No. 858,304, Mar. 25, 1992, abandoned.

[51] Int. Cl.$^5$ ............................................. A61F 2/06
[52] U.S. Cl. ........................................ 623/1; 606/198; 623/12
[58] Field of Search .................. 606/198, 200; 623/1, 623/11, 12, 900

[56] References Cited

U.S. PATENT DOCUMENTS

| | | |
|---|---|---|
| 4,776,337 | 10/1988 | Palmaz . |
| 5,015,253 | 5/1991 | MacGregor . |
| 5,019,090 | 5/1991 | Pinchuk ............................ 606/194 |
| 5,135,536 | 8/1992 | Hillstead ............................. 623/1 |
| 5,161,547 | 11/1992 | Tower ................................ 606/198 |
| 5,163,958 | 11/1992 | Pinchuk ............................ 606/198 |
| 5,314,472 | 5/1994 | Fontaine ............................. 623/1 |

Primary Examiner—C. Fred Rosenbaum
Assistant Examiner—N. Kent Gring
Attorney, Agent, or Firm—Richard J. Godlewski

[57] ABSTRACT

A vascular stent for reducing hemodynamic disturbances caused by angioplasty. The stent is formed from a single filament of low memory biocompatible material having a series of U-shaped bends. The filament is wrapped around a mandril, in a circular fashion, in order to align the curved portions of each bend which may then be connected. The stent provides a maximum amount of structural support for the lumen while minimizing hemodynamic disturbances inside the lumen.

14 Claims, 6 Drawing Sheets

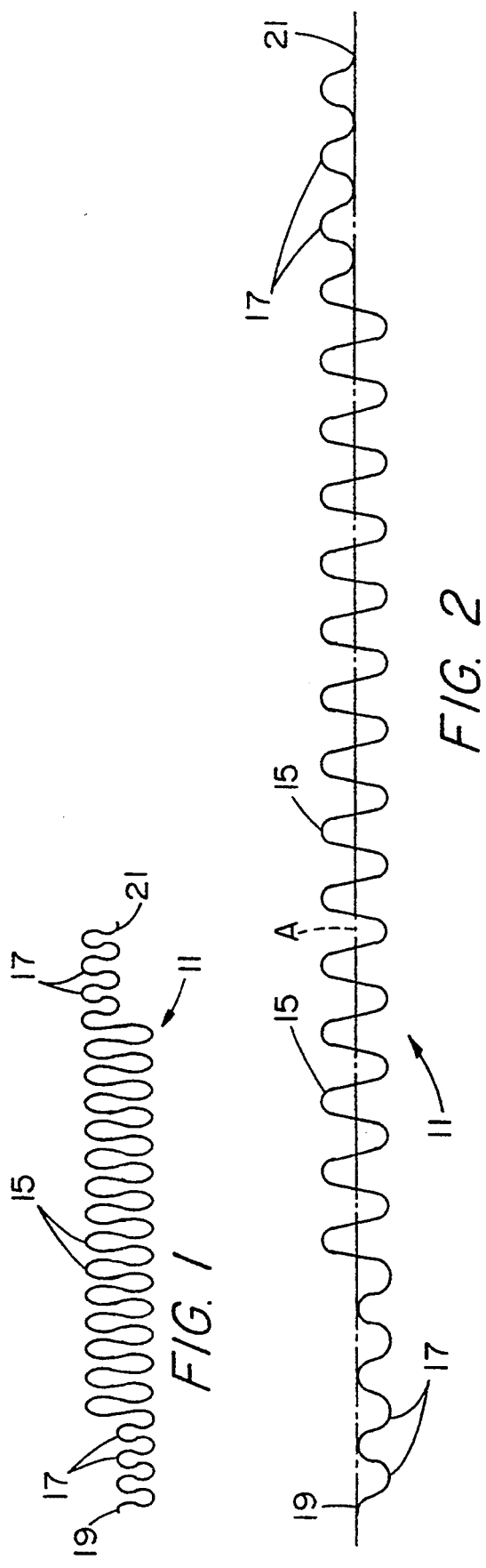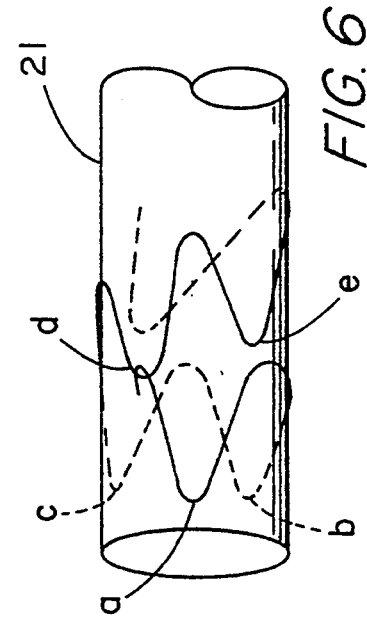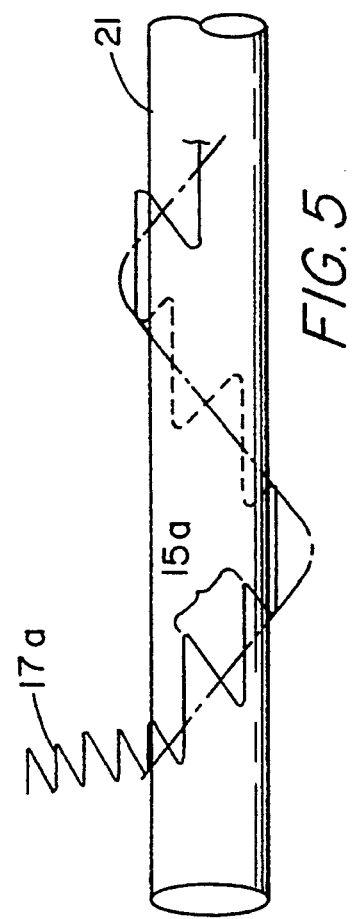

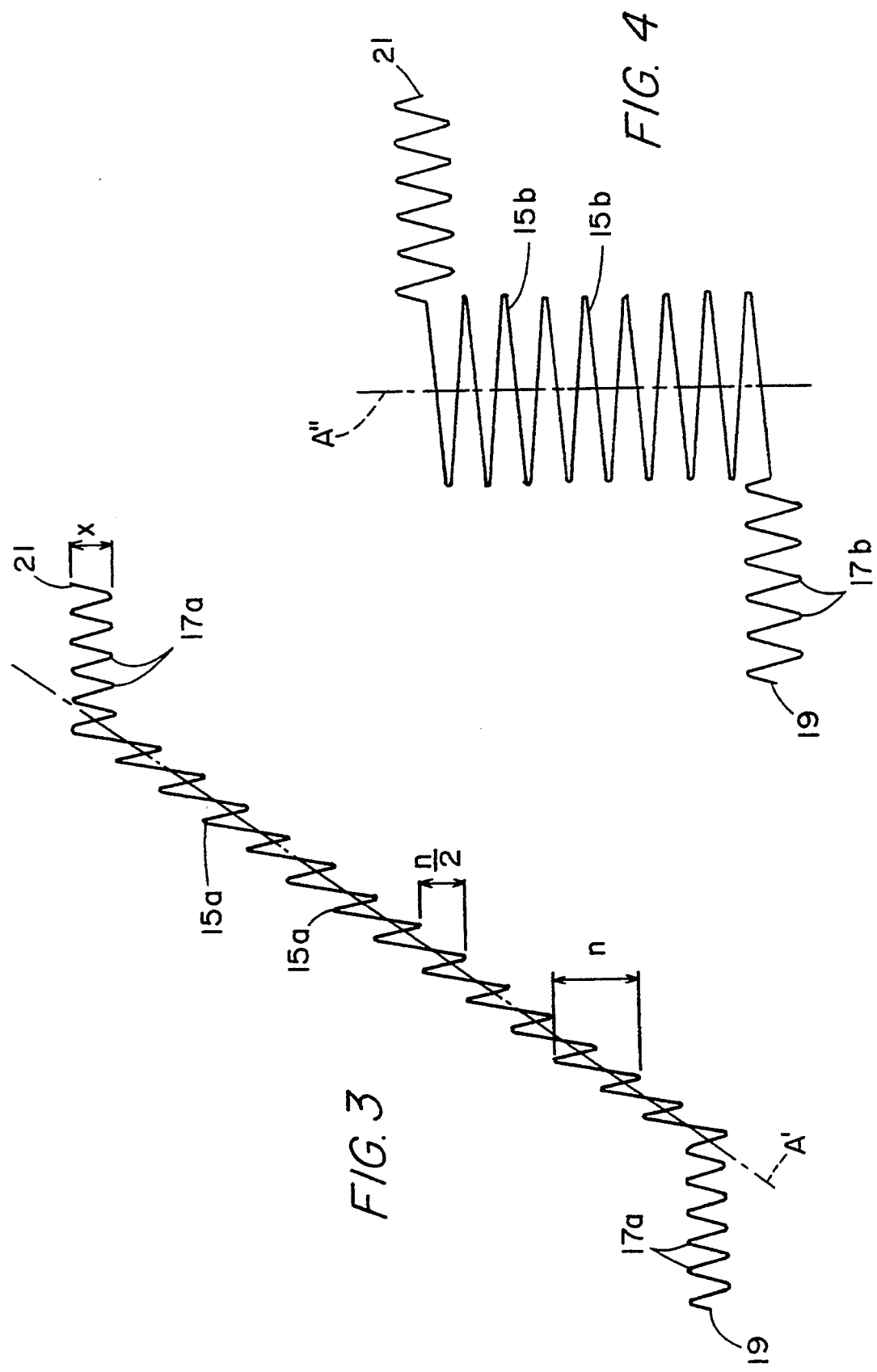

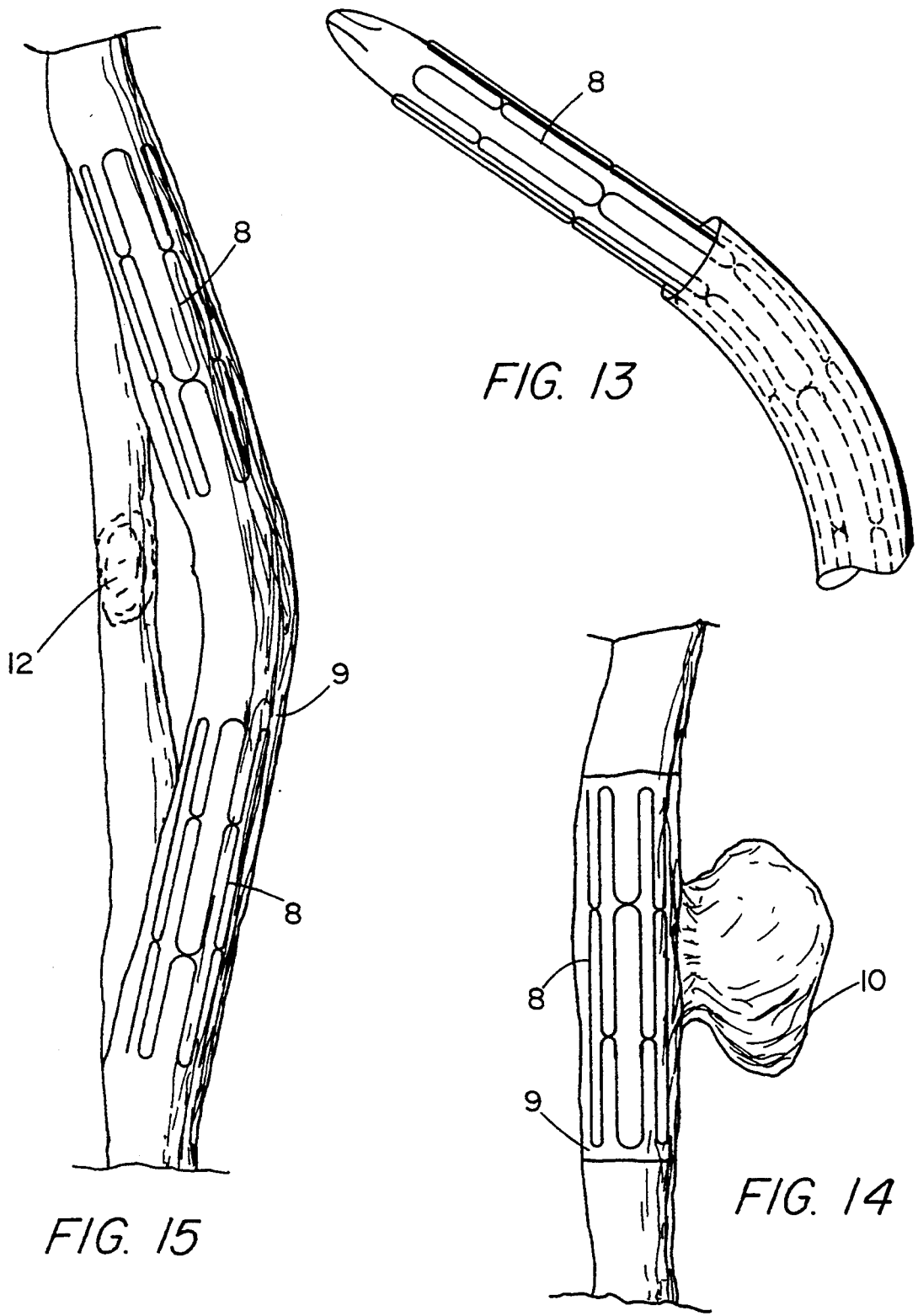

VASCULAR STENT

RELATED APPLICATION

This is a continuation of copending application(s) Ser. No. 07/858,304 filed on Mar. 25, 1992 now abandoned, which is a continuation-in-part of co-pending application Ser. No. 07/769,216, filed in the United States Patent and Trademark Office on Oct. 1, 1991, now U.S. Pat. No. 5,314,472, and commonly assigned herewith, the disclosure of which is incorporated herein in its entirety. The present application is also a parent application for copending continuation-in-part applications Ser. Nos. 07/874,347, pending filed Apr. 24, 1992, and 07/943,000, pending filed Sep. 10, 1992, both of which are commonly assigned herewith. This application is primarily related to copending design application Ser. No. 07/847,247, pending filed Mar. 9, 1992, and commonly assigned herewith. This application is also secondarily related to copending design applications Ser. Nos. 07/723,525, pending filed Jun. 28, 1991, and 07/929,150, pending filed Aug. 13, 1992, both of which are commonly assigned herewith.

BACKGROUND OF THE INVENTION

1. Field of the Invention

The present invention generally relates to vascular stents.

2. State of the Art

A stent, generally speaking, is a device that can be placed within the lumen, or interior space, of a tubular structure for supporting and assuring patency of a contracted, but otherwise intact, lumen. (Patency, the state of being freely open, is particularly important in the field of angioplasty, which is concerned with the reconstruction of blood vessels.) Stents are used, for example, for holding blood vessels open or for back tacking intimal flaps inside vessels after angioplasty. More generally, however, stents can be used inside the lumina of any physiological conduit including arteries, veins, vessels, the biliary tree, the urinary tract, the alimentary tract, the tracheobronchial tree, the genitourinary system, and the cerebral aqueduct. Furthermore, stents can be used inside lumina of animals other than humans.

In the field of angioplasty, the most common angioplasty surgical procedure is percutaneous transluminal coronary angioplasty, or "PTCA", which is employed for enlarging narrowed arteries near the heart. In a PTCA procedure, a balloon-tip catheter is maneuvered into position in a narrowed artery where the balloon is expanded in order to dilate this area of narrowing. After the arterial lumen is dilated, the balloon at the catheter tip is deflated and the catheter is removed from the enlarged artery. A vascular stent can be used to dilate an artery after a suboptimal PTCA dilation.

In practice, the above-described conventional PTCA procedure has several shortcomings. One drawback is that approximately one-third of all PTCA patients suffer from restenosis, a chronic regrowth of obstructive tissue that narrows the lumen. Typically, restenosis occurs within six months following an angioplasty procedure. Since a majority of these restenosis patients also display symptoms of deteriorating cardiac status, they frequently must undergo additional PTCA procedures or more risky coronary artery bypass graft surgery. Unfortunately, those patients who undergo repeated PTCA procedures tend to restenose at an even higher rate than first-time PTCA patients.

A second, and sometimes fatal, complication of coronary angioplasty is the abrupt re-closure of a previously dilated section of a vessel. There are many different factors that are thought to contribute to abrupt re-closure after PTCA including obstructive flaps of disrupted wall tissue, vessel wall spasms with luminal contraction, and thrombus formation at the site of dilation. Vascular stents can be used like a scaffold to mechanically bridge areas of narrowing (flaps or thrombus) and oppose spasms, and therefore, maintain artery patency.

Many of the factors responsible for abrupt closure (post balloon inflation) may also influence the development of restenosis, and therefore, long term patency. In this regard, vascular stents, by virtue of their ability to limit elastic recoil of the vessel wall and to eliminate the negative physical consequences of PTCA (including obstructing intimal flaps and dissection) may be useful in limiting restenosis.

Therefore, there are two potential benefits of vascular stents in the treatment of vascular disease: 1) prevention of abrupt arterial closure, and 2) prevention of restenosis.

SUMMARY OF THE INVENTION

Generally speaking, the present invention provides a vascular stent for reducing hemodynamic disturbances caused by angioplasty and the stent itself. In a preferred embodiment, the stent is formed from a single filament of low memory biocompatible material having a series of U-shaped bends. The filament is wrapped around a mandril in a circular fashion in order to align opposing curved portions of each bend which are then connected. The stent therefore provides a maximum amount of structural support for the lumen while minimizing the level of hemodynamic disturbance inside the lumen.

BRIEF DESCRIPTION OF THE DRAWINGS

The present invention can be further understood with reference to the following description in conjunction with the appended drawings, wherein like elements are provided with the same reference numerals. In the drawings:

FIG. 1 shows a filament shaped into a compressed planar wave used to make the nearly sinusoidal waveform of FIG. 2;

FIG. 2 shows the planar wave of FIG. 1 expanded along its longitudinal centerline to form a nearly sinusoidal waveform used in making a stent;

FIG. 3 shows an alternative waveform that can be also be used in making a stent;

FIG. 4 shows another alternative waveform that can be used in making a stent;

FIG. 5 shows the waveform of FIG. 3 spirally wrapped around a round mandril;

FIG. 6 shows a connection for the end of the filament after the waveform of FIG. 3 is completely wrapped around the mandril;

FIG. 13 shows a stent mounted on a balloon-tip catheter ready for insertion into a lumen;

FIG. 14 shows a stent being used with a graft to repair a pseudo-aneurysm in the common femoral artery;

FIG. 15 shows two stents being used with a graft to bypass an occlusion in the femoral-popliteal artery.

DESCRIPTION OF THE PREFERRED EMBODIMENTS

Figure 7:
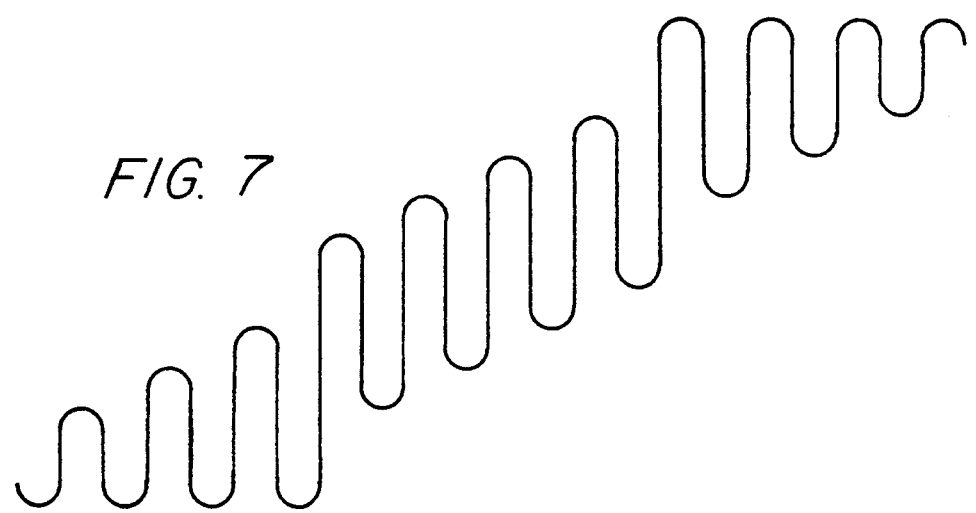
FIG. 7 shows a preferred alternative waveform that can be used in making a stent.

FIG. 1 shows a filament 11 formed in a compressed planar waveform. Preferably, the filament 11 is made from 0.005-0.020 inch diameter stainless steel wire; however, it can be made from materials such as titanium, tantalum, gold, copper and copper alloys, combinations of these materials, or any other biologically-compatible material with a low shape-memory level. (In the present context, a low shape-memory level implies that the stent will not contract to its compressed shape after it is inserted and internally expanded in a lumen.) The filament 11 can also be formed from several separate strands which are wrapped or woven together.

The compressed waveform pattern in FIG. 1 is preferably formed generally in the shape of a compressed sinusoid, but can have any wave-like pattern. In the drawing, it should be noted that the waveforms at the ends 19 and 21 of the wire having smaller amplitudes than the waveforms 15 in the middle of the wire. The drawing shows, for example, four reduced amplitude peaks 17 at each of the ends 19 and 21, respectively. Preferably, the heights of the reduced amplitude waveforms 17 are one-half to two-thirds of the heights of the larger waveforms.

In FIG. 2, the compressed waveforms of FIG. 1 are expanded along their longitudinal centerline into a nearly sinusoidal waveform by stretching the compressed waveforms from their ends. (The broken line shows the longitudinal centerline of the expanded waveforms.) At both ends 19 and 21, the longitudinal centerline of the smaller waveforms is displaced from the longitudinal centerline of the waveforms near the middle of the wire. At one end 19, for instance, the centerline of the smaller waveforms 17 is displaced below the broken line; at the end 21, by way of contrast, the centerline of the smaller waveforms is displaced above the broken line.

In practice, the above-described expanded waveforms preferably have a period of about eight millimeters. The larger waveforms 15 preferably have a peak-to-peak amplitude of eight millimeters while the smaller waveforms 17 are one-half to two-thirds the height of the larger waveforms. However, other sizes may be used. Although all of the waveforms normally have the same period, they are not necessarily sinusoidal, regular, repeating, or continuous.

FIGS. 3 and 4 show the expanded state of two alternative waveforms that can be used to form the above-described stent. The period of each waveform in the waveform of FIG. 3 is preferably one-half of the peak to peak amplitude of the waveform. In FIG. 3, the longitudinal centerlines of the small waveforms 17a at the ends of the device are approximately parallel to each other, but the centerline of the large waveforms 15a is inclined relative to the longitudinal centerlines of the smaller waveforms, preferably at an inclination angle of approximately 45°. In FIG. 4, the waveform is similar to that of FIG. 3 except that the centerline of the larger waveforms 15b is perpendicular to the centerline of the smaller waveforms 17b; in other words, the inclination angle of the larger waveforms is approximately 90°.

FIG. 5 shows the expanded waveform of FIG. 3 formed into a stent by wrapping it, in a spiral, around a mandril 21. Similar waveforms could also be used. For instance, if the waveform of FIG. 4 were used, the longitudinal centerline of the large waveforms would remain parallel to the centerline of the mandril and the peaks of the waveforms would be wrapped around the mandril, perpendicular to the centerline of the mandril.

As shown in FIG. 5, the centerline of the large waveforms 15a is arranged to spiral along the length of the mandril 21. One side of each of the larger waveforms 15a is arranged approximately parallel to the longitudinal axis of the mandril 21, and the remaining sections of each of the waveforms are arranged at a small angle to the longitudinal axis of the mandril. (In the drawing, the "small" angle has been greatly exaggerated for purposes of illustration.) It will be appreciated that the shown arrangement allows the stent to be wound in a very tight spiral.

By forming the above-described stent as a tight spiral on a mandril, the stent expands primarily in the radial direction, with relatively slight movement at the ends, as it is expanded internally in a lumen. Even greater radial expansion might be achieved by the wrapping the waveform as a circle around the mandril. However, such a radially-wrapped configuration would use an excessive amount of filament per unit surface area to support the lumen, especially where the filaments were allowed to overlap.

In FIG. 6, each of the last three smaller waveforms 17a (from FIG. 5) at the end of the stent is wrapped with its longitudinal centerline around the circumference of the mandril. It should be noted that the peaks of the last three smaller waveforms (indicated in FIG. 6 by the letters "a", "b" and "c", respectively) are approximately the same distance from the edge of the mandril, and the fourth peak "d" as well as the fifth peak "e" are slightly further away from the end of the mandril. Also, the end of the stent near peak "a" is connected to the apex of peak "d." The result of this connection is that peaks "a", "b", and "c" are substantially equally spaced around the circumference of the mandril and are all at the approximately same distance from the end of the mandril.

In practice, the connection between the loop and the filament is slidable along the filament 11, thereby allowing for radial expansion. Although this connection can be easily made using a loop as shown, it can also be made by, for example, using a bracket. The connector could also be made by brazing, welding, or gluing the end to the filament.

When the above-described stent is wound around a mandril in the shape of a tight spiral, the non-expanded form of the stent provides a profile that is lower than conventional stents, and the "tines" of the non-expanded stent are almost parallel and packed closely together. This is important because such stent can be accommodated through a smaller incision and, therefore, reduces blood loss during surgery. Furthermore, such a stent can provide an expansion ratio of about 10:1, enabling it to be used in large arteries.

Figure 12:
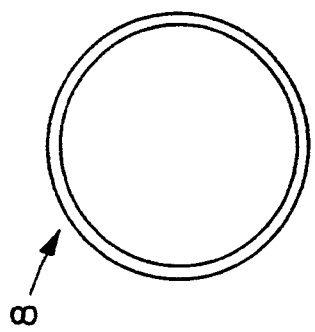
FIG. 12 shows an end view of the stents in FIGS. 10 and 11.

As shown in FIG. 12, the connections at the ends of the filament 11 create a circular hoop near each end of the stent with no sharp edges, or points, protruding from the perimeter to project into a lumen or to catch on the balloon or plaque inside of a vessel. Also, because the centerline of the smaller waveforms is arranged along the circumference of the stent, the end hoops allow the stent to fit snugly inside the lumen and prevent migration. In other words, in this arrangement, the hoops expand radially to lock the expanded stent in place in a lumen while permitting only limited longitudinal expansion.

FIG. 7 shows a preferred alternative waveform which can be used in making a stent. The waveform of FIG. 7 is formed from a series of U-shaped bends having substantially straight legs on each side of the curved portion of each "U". The legs are preferably parallel; but they may also be formed at angles to each other. The curved portions are preferably semi-circular; however, other shapes of curves can be used to connect the straight legs in each bend. The curved portions may have the same or different sizes. It is also preferred that the curved portions are connected to the straight portions at the tangent of each curve in order to prevent any discontinuities in the length of the filament.

Figure 8:
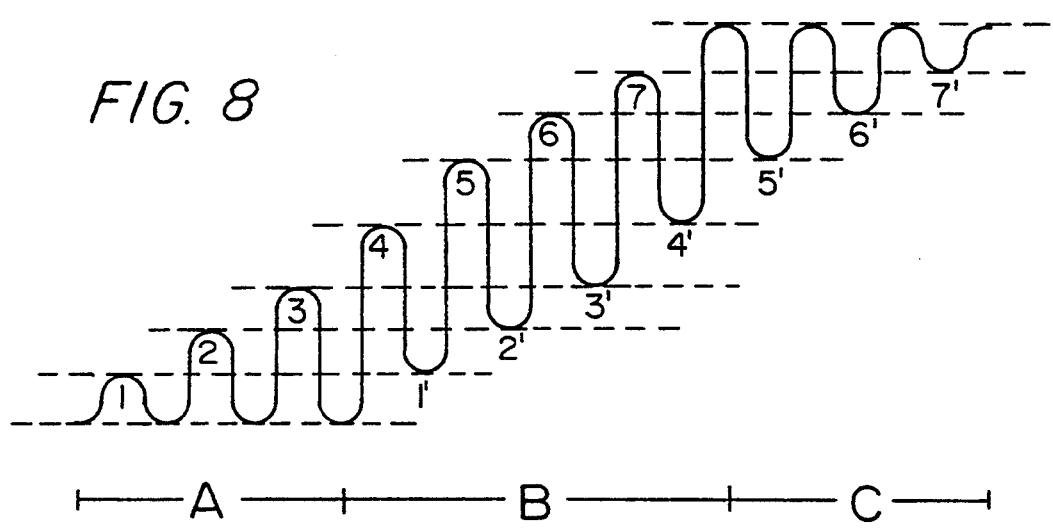
FIG. 8 shows the relative positions of the U-shaped bends in each component section of the preferred alternative waveform of FIG. 12.

FIG. 8 shows the relative positions of the U-shaped bends for each component section A, B, C of the preferred alternative waveform of FIG. 7. Sections A and C of the waveform are upside down mirror images of each other. The broken lines in FIG. 8 are reference lines which are preferably equally spaced and parallel. However, it is also possible to form the stent so that the top and bottom reference lines are parallel to each other but not equally spaced from or parallel to the other reference lines.

Defining the distance between the reference lines as one unit of measurement, then each of the U-shaped bends in end sections A and C each have a different length. For example, U-shaped bend 1 is one unit long while U-shaped bend 3 is three units long. Similarly, U-shaped bend 7' is one unit long while U-shaped bend 5' is three units long. In contrast, each of the waveforms in section B has one long leg which is four units long and one short leg which is three units long. For example, the left leg of U-shaped bend 5 is four units long while the right leg is three units long as measured between the reference lines. Each of the curved portions, except for the ends of the filament, are preferably semicircular with a diameter of one unit. The curved portion at each end of the filament is preferably one half of the semicircular arc. However, other shapes and proportions may also be used to appropriately size the stent.

Figure 9:
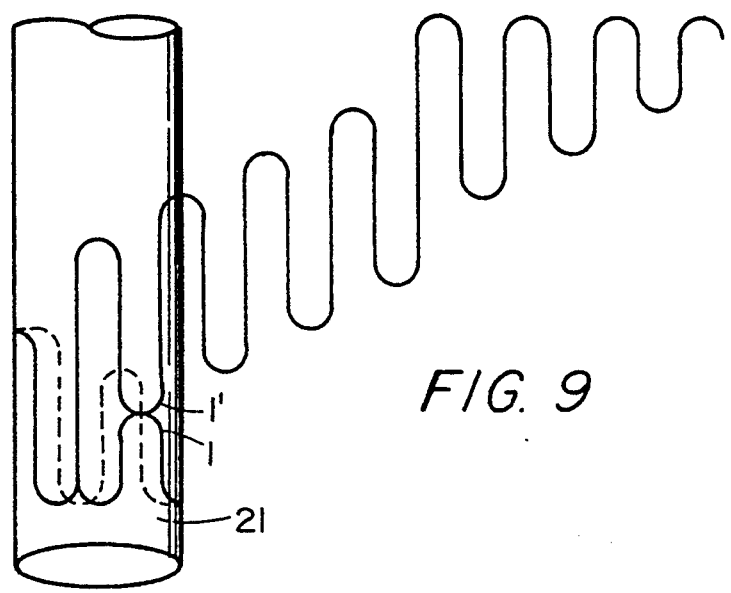
FIG. 9 shows the preferred alternative waveform of FIG. 7 being wrapped around a cylindrical mandril.

As shown in FIG. 9, the stent is formed by wrapping the waveform of FIG. 7 around a mandril which is preferably cylindrical. However, mandrils with other shapes could also be used. The waveform is preferably wrapped around the mandril so that the legs of each U-shaped bend are parallel to the axis of the mandril, which in turn results in each U-shaped bend bisected by the longitudinal axis of the mandrel. In this configuration, a single wire may be formed into an extremely rigid tubular structure with very little material to disturb flow inside the lumen. However, the waveform might also be wrapped around the mandril in a slightly spiral manner. Once the waveform is wrapped around the mandril, the outside edge of curves on the same reference line will be arranged back-to-back adjacent to (or overlapping with) each other. As shown in FIGS. 7-10, the stent is made from a single strand of continuous wire which does not cross over itself over the length of stent. For example, the outside edge of curve 1 will be back-to-back with the outside edge of curve 1'. Similarly, the outside edge of curve 7 will be adjacent to curve 7'. The outside edges of these U-shaped bends can then be fastened together by any conventional means such as welding, brazing, soldering, or gluing.

Figure 10:
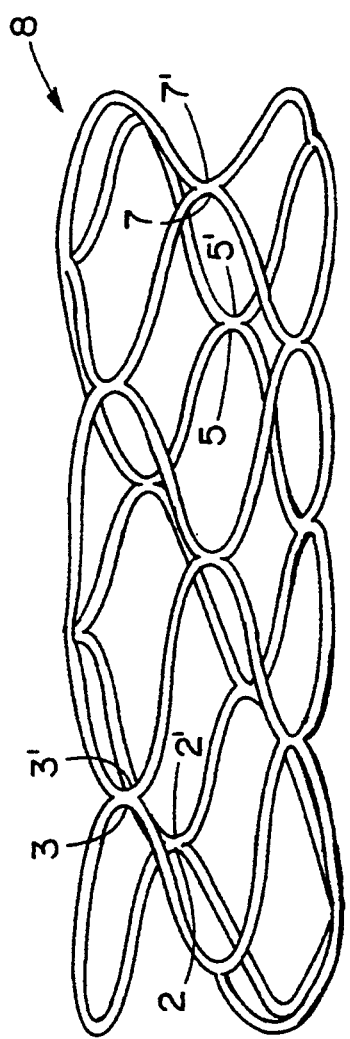
FIG. 10 shows a side elevation of a stent formed from the preferred alternative waveform of FIG. 7 by wrapping it around a mandril in a circular fashion in order to align the curved portion of each bend.
Figure 11:
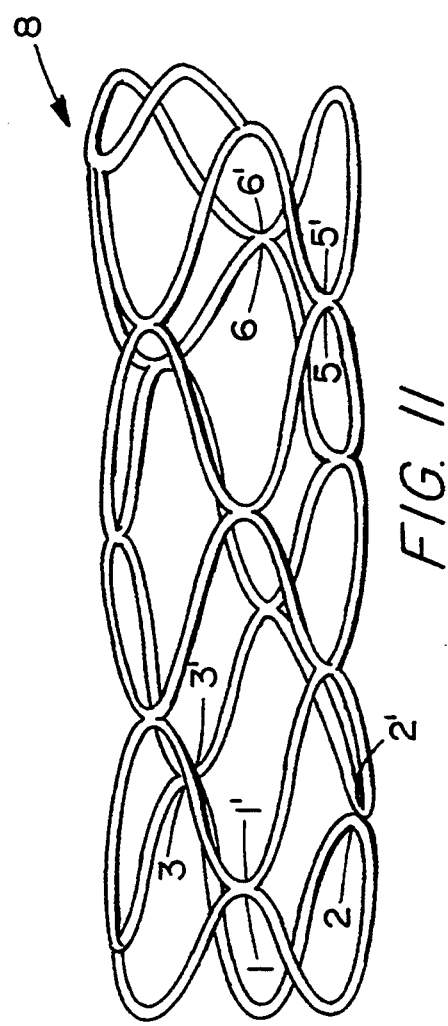
FIG. 11 shows an opposite side elevation of the stent in FIG. 10.

FIGS. 10, 11, and 12 illustrate the stent which is formed by wrapping the waveform of FIG. 8 around a circular mandril with the reference lines arranged on the circumference of the mandril. It will be apparent that each of the labeled U-shaped bends on parallel reference lines in FIG. 8 have been connected in FIGS. 10 and 11. For example, U-shaped bend 7' is shown to be connected to U-shaped bend 7 at the top of FIG. 10. Although it is preferred that the U-shaped bends are welded, it is also possible to form the connecting portions of the filament from a single piece of material in order to eliminate the need for connecting each of the appropriate U-shaped bends. The ends of the filament are also connected back to the filament and trimmed in order to remove any excess filament precluding from the free end.

The rigidity of the structure may be controlled by welding less than all of the adjacent curved portions. For example, a stent with only half the U-shaped portions welded together would be approximately half as rigid as a stent with all the tangent points welded together. Of course, the stent can also be used without any connections between adjacent curved portions.

The lowest possible profile (i.e., diameter) is provided by arranging the long leg of each U-shaped bend parallel to the axis of the catheter before it is inserted into a lumen. This arrangement increases the diameter to which the stent can be expanded without, at the same time, decreasing the end-to-end length of the stent. By increasing or decreasing the length of the long leg of each U-shaped bend, one can alter the expansion ratio without altering the profile. Consequently, a nearly unlimited circumferential expansion ratio may be created without contracting the stent along its longitudinal axis. The expansion ratio is therefore nearly independent of this profile.

When expanded, each of the U-shaped portions in the stent may assume a rhomboidal pattern where the legs of each U-shaped bend are no cell longer parallel. As shown in FIGS. 10 and 11, a plurality of rhomboidal cells are distributed around the cylindrical surface defined by the stent. Furthermore, because the legs alternate in length over the middle portion of the waveform as shown in FIG. 8, each adjacent leg of each rhomboidal cell differs in length. The expansion ratio of the stent may therefore exceed 10 to 1 in terms of the expanded diameter versus the unexpanded diameter of the stent. Consequently, the outside surface of the stent touching the vessel is small while the effective support area is very large. This feature dramatically reduces the possibility of causing any hemodynamic disturbances inside the vein or artery because of the stent. The large expansion ratio also allows the stent to be used with smaller incisions. Moreover, this configuration allows the stent to be flexible in the radial direction in order to accommodate the pulsation of an artery.

The stent may also be coated with anti-thrombolytic agents in order to limit the thrombotic formation which often accompanies angioplasty.

FIGS. 13–16 illustrate a typical stent of which could represent any one of the embodiments described above. FIG. 13 shows a typical stent mounted on a 4/5 F balloon (4–10 mm) with a 6/7 F sheath. The apparatus of FIG. 13 is preferably used with a 0.078–0.091 guide sheath. FIG. 14 shows the stent, inside a graft, being used to repair a pseudo-aneurysm in a common femoral artery. The stent 8 is placed inside graft 9 which blocks off pseudo-aneurysm 10. Although the stent is shown to be completely inside graft 9, it may also extend outside the edges of the graft in order to provide additional support for the incisions at the end of the graft.

Figure 16:
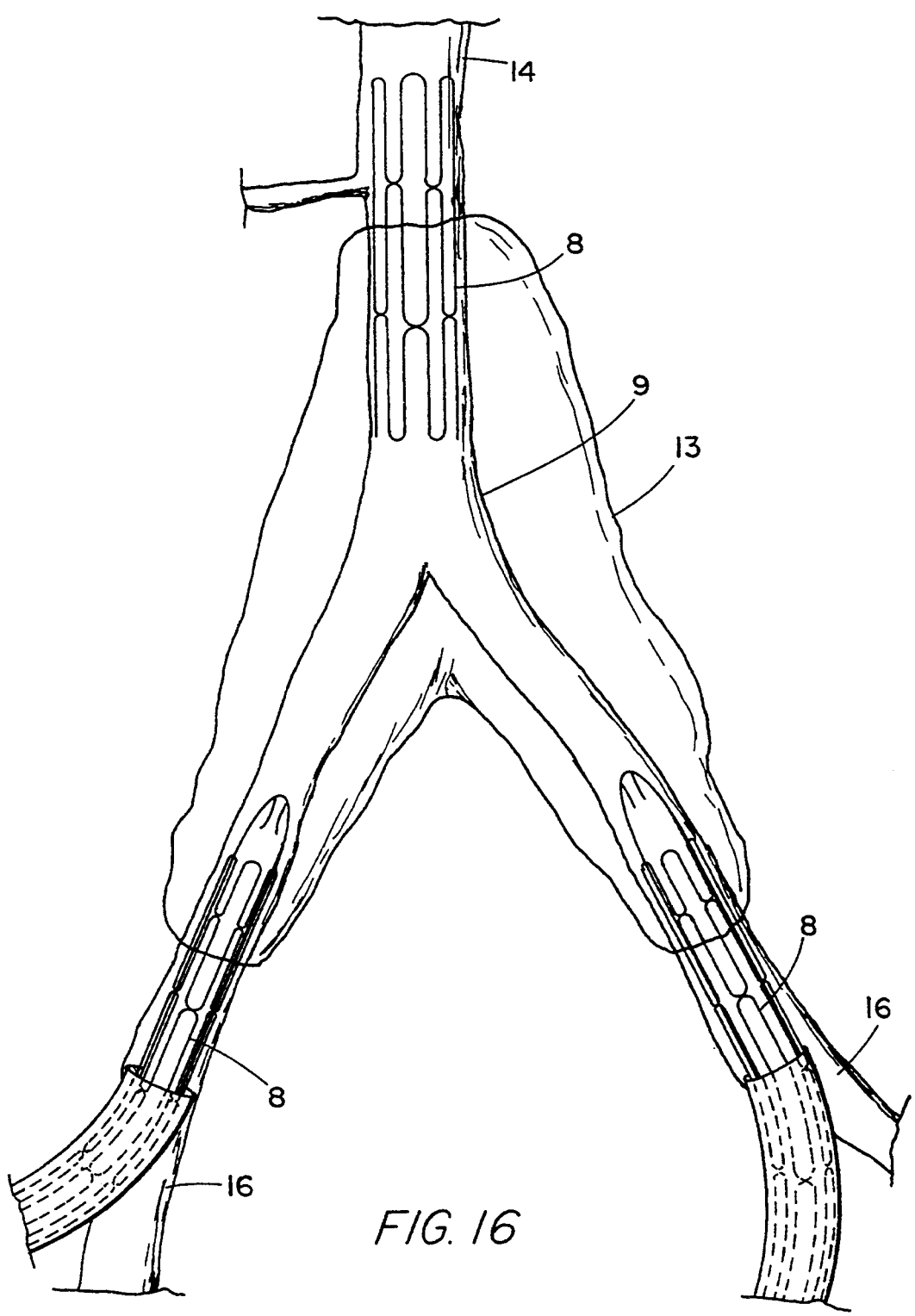
FIG. 16 shows a stent being used with a graft to repair an aorto-iliac aneurysm.

FIG. 15 shows two stents being used at each end of a graft to bypass an occlusion 12 in, for example, the femoral-popliteal artery. FIG. 16 illustrates how three stents can be used with a branched graft to repair an aorto-iliac aneurysm 13. The graft 9 is placed inside the aneurysm and secured at one end to the aorta 14. The other ends of the graft are similarly stented to iliac branches 16.

FIG. 16 also illustrates how the catheter holding the stent can be used to insert the stent 8 inside a lumen. Typically, a short incision is made in the lumen (for example, a vein or artery) and the stent, which is mounted on the balloon, is then slipped into the incision. When the stent is in place, the balloon is expanded in order to expand the stent against the inside walls of the lumen. Once the stent is in place, the balloon is deflated and removed through the inside of the stent and the incision in order to leave the stent in place.

Various advantages of the present invention can now be understood. For example, the above-described stent uses substantially less material than conventional stents (especially knitted ones with overlapping wires) and, therefore, introduces a substantially lesser quantity of foreign material into a lumen. The stent also provides a maximum amount of structural support with a minimum amount of material. As another example, the above-described stent connects its filament ends back onto the filament to prevent thrombosis in blood vessels or damage to any type of a lumen wall such as is caused by stents that have loose wire ends that protrude into a lumen.

Another advantage of the above-described stent is that it provides substantial radial expansion with only limited longitudinal migration and, therefore, reduces the problem of migration inside a lumen. More particularly, the hoops and end component sections at each end of the above-described stent reduce migration by securing the stent inside of a lumen. In the preferred embodiment, the hoops, end component sections, as well as the spiral shape of the stent itself are oriented to inhibit longitudinal growth of the stent during radial expansion.

Yet another advantage of the above-described stent is that it provides sufficient flexibility to allow implantation in tortuous lumens and in applications where lumen bending is required. This overcomes the problem with conventional stents that are so stiff that they are difficult to negotiate through a tortuous vessel during implantation. Furthermore, a stiff stent can cause damage to certain vessels, such as those around joints, that require flexibility.

The foregoing has described the principles, preferred embodiments and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A stent having a longitudinal axis comprising:
   a continuous filament shaped into a waveform pattern having a plurality of substantially straight legs connected by U-shaped bends, consecutive ones of said straight legs varying in length, said waveform pattern being spirally wrapped about said axis to define a cylindrical surface in which a plurality of said U-shaped bends are in tangential contact;
   said straight legs being substantially parallel to said longitudinal axis when the stent is in a radially compressed state;
   said U-shaped bends being substantially bisected by said longitudinal axis; and
   a plurality of pairs of said U-shaped bends that are in tangential contact being attached together in a non-overlapping manner so that said cylindrical surface includes a plurality of rhomboidal cells bounded on all four sides by said substantially straight legs.

2. The stent of claim 1 wherein said continuous filament is a single strand of wire and the stent is made without said wire crossing over itself.

3. The stent of claim 2 wherein said consecutive ones of said straight legs alternate in length over a portion of said waveform pattern.

4. A stent having a longitudinal axis comprising:
   a continuous filament shaped into a waveform pattern having a plurality of substantially straight legs connected by U-shaped bends, consecutive ones of said straight legs varying in length, said waveform pattern being wrapped about said axis to define a cylindrical surface; and
   a plurality of pairs of said U-shaped bends being attached together in a non-overlapping manner so that said cylindrical surface includes a plurality of rhomboidal cells bounded on all four sides by said substantially straight legs.

5. The stent of claim 4 wherein said straight legs are substantially parallel to said axis when the stent is in a radially compressed state.

6. The stent of claim 5 wherein said waveform pattern is spirally wrapped about said axis.

7. The stent of claim 5 wherein said waveform pattern includes a portion in which at least four successive straight legs alternate in length.

8. The stent of claim 4 wherein said continuous filament is a single strand of wire and the stent is made without said wire crossing over itself.

9. A stent having a longitudinal axis comprising:
   a continuous filament shaped into a waveform pattern having a plurality of substantially straight legs connected by U-shaped bends, consecutive ones of said straight legs varying in length, said waveform pattern being spirally wrapped about said axis to define a cylindrical surface;

said straight legs being substantially parallel to said longitudinal axis when the stent is in a radially compressed state; and said U-shaped bends being substantially bisected by said longitudinal axis.

10. The stent of claim 9 wherein said consecutive ones of said straight legs alternate in length over a portion of said waveform pattern.

11. The stent of claim 10 wherein at least one pair of said U-shaped bends is attached together to define an attachment.

12. The stent of claim 11 wherein said at least one pair of said U-shaped bends is attached together in a non-overlapping manner and wherein a plurality of said attachments result in the stent having at least one rhomboidal cell bounded on all sides by said straight legs.

13. The stent of claim 12 wherein said continuous filament is a single strand of wire and the stent is made without said wire crossing over itself.

14. A method of forming a stent comprising the steps of:

forming a continuous filament into a waveform pattern having a plurality of substantially straight legs connected by U-shaped bends, consecutive ones of said straight legs alternating in length;

wrapping the waveform pattern around a cylindrical mandrel so that some of the U-shaped bends are arranged back to back in tangential contact; and connecting in a non-overlapping manner at least some of the U-shaped bends in tangential contact.

* * * * *